US010107759B2

(12) United States Patent
Bergsch

(10) Patent No.: US 10,107,759 B2
(45) Date of Patent: Oct. 23, 2018

(54) OPTICAL EMISSION SPECTROSCOPE WITH A PIVOTABLY MOUNTED INDUCTIVELY COUPLED PLASMA SOURCE

(71) Applicant: Spectro Analytical Instruments GmbH, Kleve (DE)

(72) Inventor: Manfred A. Bergsch, Kleve (DE)

(73) Assignee: Spectro Analytical Instruments GmbH, Kleve (DE)

( * ) Notice: Subject to any disclaimer, the term of this patent is extended or adjusted under 35 U.S.C. 154(b) by 0 days.

(21) Appl. No.: 15/535,977

(22) PCT Filed: Dec. 15, 2014

(86) PCT No.: PCT/EP2014/077782
§ 371 (c)(1),
(2) Date: Jun. 14, 2017

(87) PCT Pub. No.: WO2016/095948
PCT Pub. Date: Jun. 23, 2016

(65) Prior Publication Data
US 2017/0343478 A1   Nov. 30, 2017

(51) Int. Cl.
*G01T 3/00* (2006.01)
*G01N 21/68* (2006.01)
(Continued)

(52) U.S. Cl.
CPC .............. *G01N 21/68* (2013.01); *G01J 3/443* (2013.01); *G01N 21/73* (2013.01); *H01J 49/105* (2013.01); *H01J 49/34* (2013.01)

(58) Field of Classification Search
CPC .. G01N 21/35; G01N 21/359; G01N 21/3504; G01J 3/02; G01J 3/42
See application file for complete search history.

(56) References Cited

U.S. PATENT DOCUMENTS 6,222,186 B1   4/2001  Li et al.
2012/0325783 A1  12/2012  Morrisroe

FOREIGN PATENT DOCUMENTS

EP        0708324 A2      4/1996
JP     2011227054 A   *  11/2011

OTHER PUBLICATIONS

Translation of JP 2011227054 A.*
(Continued)

*Primary Examiner* — Edwin Gunberg
*Assistant Examiner* — Mamadou Faye
(74) *Attorney, Agent, or Firm* — Panitch Schwarze Belisario & Nadel LLP

(57) ABSTRACT

An optical emission spectrometry instrument may comprise an inductively coupled plasma generator (ICP) with an electromagnetic coil having input and ground connectors. The electromagnetic coil may be mounted to a mounting disk, and the input connector may be coupled to a power output of a radio frequency power source, and the ground connector may be connected to the mounting disk. A spectro-chemical source may be used for sample excitation. The spectro-chemical source and the ICP may have a longitudinal axis. An optical system may be included for viewing the spectro-chemical source with a fixed view axis. The electromagnetic coil may be mounted pivotably around one of its connectors so that the orientation of the ICP can be altered from a first orientation of its longitudinal axis to a second orientation of its longitudinal axis, and vice versa.

9 Claims, 1 Drawing Sheet

(51) Int. Cl.
H01J 49/10 (2006.01)
G01N 21/73 (2006.01)
G01J 3/443 (2006.01)
H01J 49/34 (2006.01)

(56) References Cited

OTHER PUBLICATIONS

Int'l Preliminary Report on Patentability dated Jun. 20, 2017 in Int'l Application No. PCT/EP2014/077782.
Nakamura et al, "Evaluation of an Axially and Radially Viewed Inductively Coupled Plasma Using an Echelle Spectrometer With Wavelength Modulation and Second-Derivative Detection," Journal of Analytical Atomic Spectrometry, vol. 9, pp. 751-757 (1994).
Int'l Search Report dated Aug. 17, 2015 in Int'l Application No. PCT/EP2014/077782.
Monnig et al, "Tomographic Image Reconstruction Techniques for Spectroscopic Sources-II. Instrumentation," Spectrochimica Acta., vol. 45B, No. 3, pp. 261-270 (1990).
Written Opinion dated Aug. 17, 2015 in Int'l Application No. PCT/EP2014/077782.

* cited by examiner

OPTICAL EMISSION SPECTROSCOPE WITH A PIVOTABLY MOUNTED INDUCTIVELY COUPLED PLASMA SOURCE

CROSS-REFERENCE TO RELATED APPLICATIONS

This application is a Section 371 of International Application No. PCT/EP2014/077782, filed Dec. 15, 2014, which was published in the English language on Jun. 23, 2016, under International Publication No. WO 2016/095948 A1 and the disclosure of which is incorporated herein by reference.

BACKGROUND OF THE INVENTION

The present invention relates to an optical emission spectrometer having the features of the preamble of Claim 1 and a method of optical emission spectrometry having the features of the preamble of Claim 9.

The most important example of a spectro-chemical source for sample excitation in the context of emission spectrometry with no doubt is the inductively coupled argon plasma at atmospheric pressure (ICP). The ICP as spectro-chemical source for optical emission spectroscopy (OES) was introduced, in the form of commercially available instruments, in the early 1970s. Depending on the actual spectrometer optics utilized in conjunction with the plasma source, a high analysis efficiency could be achieved, especially by simultaneously measuring many emission lines in the emission spectrum generated by the spectro-chemical plasma source (or even the 'complete' emission spectrum), therefore simultaneously determining many or almost all elements present in the sample.

This capability, together with good sensitivity and a large dynamic range allowing to analyze element concentrations from trace to major component level in a wide variety of samples, made optical emission spectrometry with a spectro-chemical plasma source a nearly immediate success, becoming one of the workhorses of inorganic analysis ever since.

The first commercially available ICP-OES instruments employed a vertically oriented ICP, viewed from the side ('radially' or 'side-on') by the emission spectrometer optics. This configuration allows for good system robustness, allowing analyzing, without much system optimization work, of a multitude of sample types, from aqueous samples, samples with high totally dissolved solids and brines to organic samples, even including highly volatile chemicals. However, due to the limited path length observed in the spectro-chemical source in radial direction, the achievable limits of detection were sometimes inferior to other methods of spectro-chemical analysis, especially compared to graphite furnace atomic absorption spectrometry (GF-AAS).

The latter only changed in the beginning of the 1990s, with the commercial availability of the first ICP-OES instruments employing an axially viewed plasma ('end-on plasma'), with a horizontal orientation of the spectro-chemical plasma source (ICP). The longer observed path length in the spectro-chemical plasma source axially ('end-on') viewed by the spectrometer optics leads to an improvement of the achievable limits of detection by a factor of between ca. 2 and 50, compared to the radial ('side-on') plasma observation, also depending on the element to be analyzed and the emission line to be used.

While axially ('end-on') viewing the horizontally oriented spectro-chemical plasma source improved the achievable limits of detection, for certain analyte elements (most notably alkaline and earth-alkaline elements), the measurement linearity over the available dynamic range is poorer, compared to radially ('side-on') viewing the spectro-chemical plasma source, mainly as result of the so-called 'easily ionizable elements effect' (EIEE) shifting the ionization balance in the spectro-chemical plasma source. Occurrence of the EIEE is of course independent from both the spatial orientation of the spectro-chemical plasma source and the observation direction of the optical system utilized, but due to the different optical path lengths employed in radial ('side on') or axial ('end on') viewing of the plasma source, its influence on the analytical results is only relevant in the axially ('end-on') viewing set-up, where it can lead to measurement inaccuracies of up to several hundred percent, for the elements affected by it, if no special pre-cautions, e.g. usage of an ionization buffer, are employed.

A solution to the non-linearities observed in emission spectrometry with an axially ('end-on') viewed spectro-chemical plasma source (typically having the source in horizontal orientation) was the addition of a second light path to the optical system, allowing to view the spectro-chemical plasma source also in radial ('side-on') direction, sequentially or semi-simultaneously, e.g. by observing emissions of the spectro-chemical plasma source axially ('end-on') for one spectral range and radially ('side-on') for another one. Such 'dual observation' systems allow analyzing elements not affected by the EIEE in axial ('end-on') view, with its improved limits of detection, and then (typically sequentially) switching light paths to radial ('side-on') observation, analyzing the elements affected by the EIEE with the improved linearity that the radial ('side-on') observation of the spectro-chemical plasma source emission is able to provide.

'Dual observation' systems of the described kind are known in the prior art e.g. from EP 0 708 324 A2 and are commercially available, utilizing a single, spatially fixed orientation of the spectro-chemical source, relative to the optical system view axis, and two observation light paths, for emission transfer from the spectro-chemical source into the optical system, with these observation light paths oriented orthogonally to the spatially fixed spectro-chemical plasma source, and allowing to view the spectro-chemical plasma source in either axial or radial direction, depending on user choice and analytical requirements, e.g. by employing switchable optical elements in the light paths.

Typically, single orientation dual light-path ('dual observation') systems are designed as axially ('end-on') viewed systems, often with horizontal orientation of the spectro-chemical plasma source, and having additional radial ('side-on') view capability. As an example, attempting applications demanding a vertical orientation of the spectro-chemical plasma source and radial ('side-on') observation (e.g. high TDS or organic samples) on such a system typically will, depending on the analytical task at hand, result in compromised performance, usually not comparable to the capabilities of a corresponding single-orientation, single light-path system, which in this case would have a vertically oriented spectro-chemical plasma source viewed in radial ('side-on') direction.

Alternatively, 'dual observation' systems employing a (fixed) vertical orientation of the spectro-chemical plasma source have become commercially available, but are also expected being limited in typical vertical source/radial view applications, by the required presence of an optical interface or a similar mechanism, allowing to observe the emission of the vertically oriented spectro-chemical plasma source in an axial ('end-on') direction.

The article "Evaluation of an Axially and Radially Viewed Inductively Coupled Plasma Using an Échelle Spectrometer With Wavelength Modulation and Second-derivative Detection" (Journal of Analytical Atomic Spectrometry, July 1994, Vol. 9, pages 751-757) by Nakamura et al. discloses the computer controlled movement of the ICP torch assembly between end-on and side-on measurements in a scientific approach. How the movement is carried out can neither be learnt from the description nor the figures.

BRIEF SUMMARY OF THE INVENTION

It is the object of the present invention to provide an optical emission spectrometry system with a spectro-chemical source whose spatial orientation to a view axis of an optical system is not fixed at the time of the emission spectrometry system's manufacture, but can be changed easily by the user to be suitable in an industrial environment and according to analytical requirements, providing improved system performance for the entirety of conceivable optical emission spectrometry applications.

This object is achieved by an optical emission spectrometer having the features of Claim 1 and a method of optical emission spectrometry having the features of Claim 9.

According to the present invention, an optical emission spectrometry instrument comprising an inductively coupled plasma generator (ICP) with an electromagnetic coil having a first connector and a second connector,
wherein the electromagnetic coil is mounted to a mounting disk and
the first connector is coupled to a power output of a radio frequency power source and
the second connector is connected to the mounting disk,
and with a spectro-chemical source for sample excitation, wherein the spectro-chemical source and the inductively coupled plasma generator have a longitudinal axis,
and with an optical system viewing said spectro-chemical source with a fixed view axis,
is provided for, whereas the electromagnetic coil is mounted pivotably around one of its connectors so that the orientation of the inductively coupled plasma generator can be altered from a first orientation of its longitudinal axis, which is parallel to the fixed view axis of the optical system to a second orientation of its longitudinal axis, which is perpendicular to the fixed view axis of the optical system and vice versa. The optical emission spectrometry systems' spatial orientation to the view axis of the optical system is not fixed at the time of the emission spectrometry system's manufacture. It can be changed easily by the user to be suitable in an industrial environment and according to analytical requirements, it provides improved system performance for the entirety of conceivable optical emission spectrometry applications. Finally, availability of such a system results in substantial cost saving for the end user, by not having to acquire two different emission spectrometry systems, with different orientations of the spectrochemical source to the optical system's view axis, for optimum analytical capabilities for 'all' conceivable emission spectrometry applications. The spatial orientation to the view axis can be changed around a pivot axis defined by the first connector or the second connector of the electromagnetic coil.

Both connectors can be coupled symmetrically to a power source, so that both connectors can be viewed as input connectors. It is, however, preferred that the first connector is a power input connector, and that the second connector is a ground connector, so that the second connector is essentially at ground potential while the coil is powered.

In a preferred embodiment the electromagnetic coil is mounted pivotably around its input connector. Further it can be preferred, that the ground connector of the electromagnetic coil is coupled to the mounting disk and that the mounting disk has a sliding contact connected to the ground potential of the instrument. Theoretically the potential difference between the output of the electromagnetic coil and the ground should be zero, because the output of the radio frequency power source is ideally totally dissipated in the plasma. Therefore, the sliding contact is preferably used for the ground connector.

More preferably, the inductively coupled plasma generator is arranged on a rotatable disc, whereas the disc rotates around its center which coincides with the coil input connector rotation axis.

In a more specific embodiment, the coupling of the input connector to the power output is a rotatable coupling allowing for a relative rotation of at least 90°.

The inductively coupled plasma generator can be operated in Argon at atmospheric pressure (ICP).

In a preferably embodiment, it is defined, that in the second orientation, in which the longitudinal axis is perpendicular to the fixed view axis of the optical system, the distance between the view axis and the coil equals the radius of the coil. Furthermore it is preferable, that in the first orientation the longitudinal axis coincides with the fixed view axis of the optical system.

According to the present invention, further, a method of optical emission spectrometry is provided for, comprising the steps of exciting a sample in a spectro-chemical plasma source of an inductively coupled plasma generator with an electromagnetic coil and a longitudinal axis to emit characteristic radiation, and observing the emitted radiation by an optical system with a fixed viewing axis, whereas the orientation of the inductively coupled plasma generator can be altered from a first orientation of its longitudinal axis, which is parallel to the fixed view axis of the optical system to a second orientation of its longitudinal axis, which is perpendicular to the fixed view axis of the optical system and vice versa by swiveling the inductively coupled plasma generator around a pivot axis defined by the electromagnetic coil.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
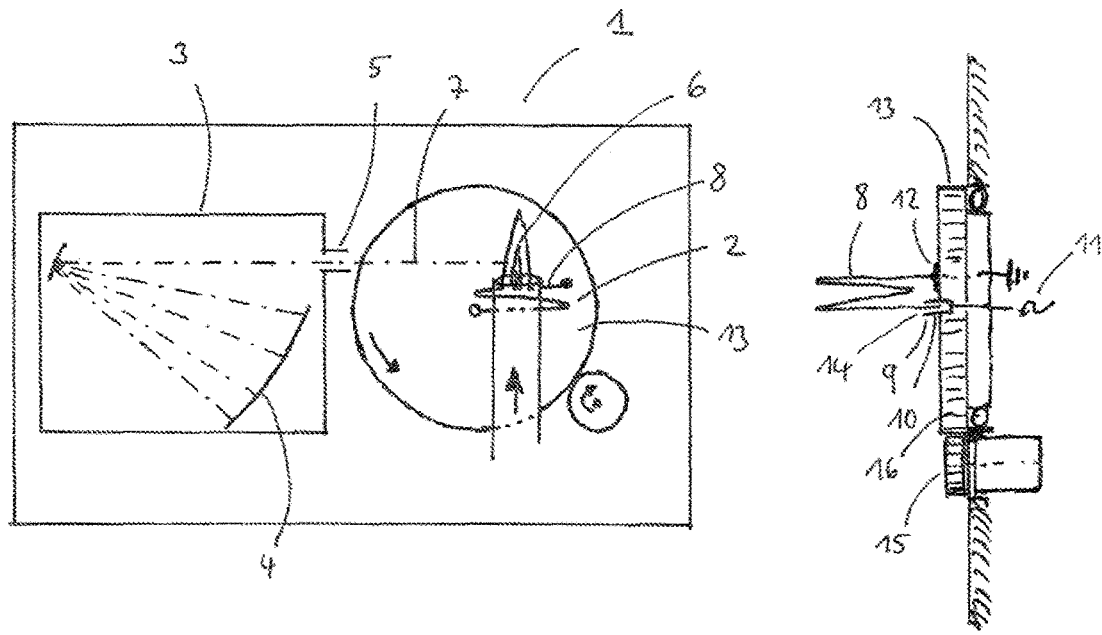
FIG. 1 shows a schematic diagram of a side-on arrangement of an optical emission spectrometer in top and side view and FIG. 2 shows a schematic diagram of an end-on arrangement of the atomic emission spectrometer in top and side view.
Figure 2:
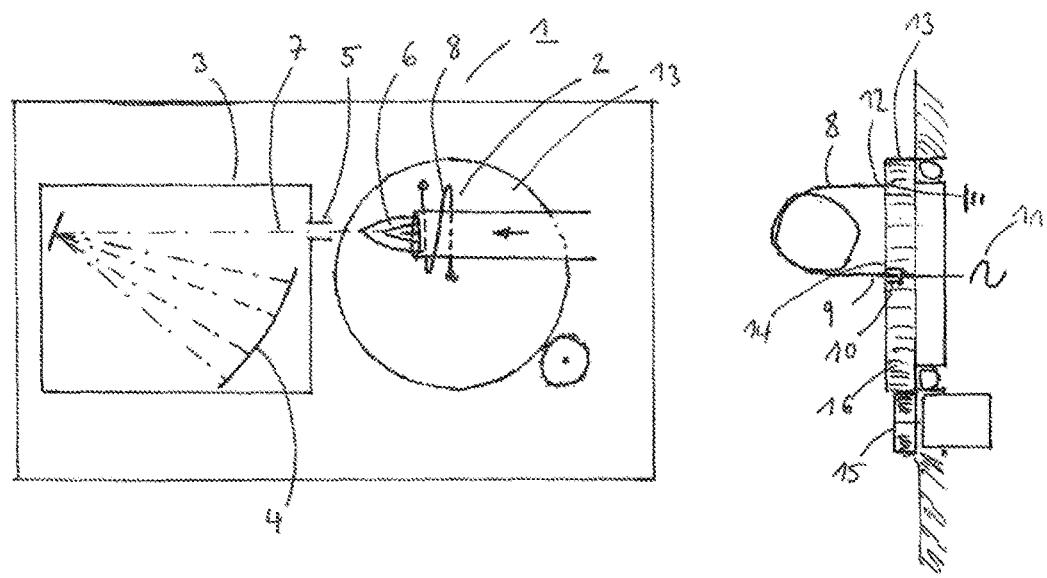

In FIGS. 1 and 2, an optical emission spectrometer 1 with a user-selectable source view mode is schematically illustrated in side-on and end-on setting. The relative sizes of the components are not realistic. In reality, the spectrometer part is much larger than the source components. The optical emission spectrometer 1 shows three general components, an inductively coupled plasma generator 2 which effects ultraviolet and visible light radiation, a spectrometer 3 with a detector means 4 for detecting the radiation relative to spectral wavelength and an intermediately located interface 5 from which a constant flow of argon emerges, deflecting the plasma and providing cooling. In addition, the flow of Argon purges the optical path and removes Nitrogen and Oxygen, both absorbing UV radiation if present, thus allowing the full spectrum of the emitted light from the plasma 6 to enter the spectrometer 3 along a spectrometer optics view axis 7. The inductively plasma generator (ICP) 2 utilizes an electromagnetic coil 8 to excite a gas into a plasma in a region within or slightly beyond the end of a quartz tube. The generator 2 includes an injector for injecting a nebulized sample material into the plasma. The material becomes dissociated to atoms which are, by means of the plasma, transferred into an excited state to emit radiation including spectral lines characteristic of the atomic elements in the sample. The detector means 4 includes a detector system which may be any conventional or other desired type used for the purpose of the spectrometer, e.g. solid state CCD detector which effects signals proportional to the intensity of the corresponding lines. A computer subsequently processes the signal information, corrects for background and, with calibration, displays the results on a monitor.

The electromagnetic coil 8 of the ICP 2 includes a radio frequency (RF) power input 9 coupled to the power output 10 of a RF power source 11, and an output 12 being grounded.

The coil 8 and thus the inductively coupled plasma generator 2 is arranged off-centered on a rotatable mounting disk 13. The RF power input 9 of the coil 8 is arranged in the center of the mounting disk 13 and is coupled, via a co-axial twistable RF coupling 14, to the power source 11.

In order to change the orientation of the ICP source 2, the disk 13 can be rotated by 90 degrees around its center. Hence, the coil 8 is tilted likewise by 90 degrees around its power input 9. The RF coupling 14 allows the input 9 of the coil to rotate against the power output 10 of the RF generator 11. The ground connection 12 of the coil 8 is connected to the mounting disk 13 at a point distant from the center. The mounting disk 13 itself is grounded to the ground potential of the instrument by means of a sliding contact with a large contact surface.

The rotation of the disk 13 can be carried out manually by operating a toothed rotary knob 15 which interlocks with teeth 16 arranged circumferentially of the disk 13. In another alternative, a stepper motor for rotating the disk via a gear drive can be provided. Since the necessary angle of rotation of the ICP source is limited to 90° or a little more, it is also possible to effect the rotation from a horizontal position to an upright position of the axis of the ICP coil using a push rod or lever which is eccentrically attached to the disk.

By rotation of the disk 13, the spatial orientation of the source 2 relative to the view axis 7 of the spectrometer 3 can be changed from axially to radially and vice versa.

When changing the spatial orientation it might be necessary to adjust or exchange the interface 5 and quartz tube, which can be done manually.

An easily industrially applicable user selectable spatial orientation of the spectro-chemical source relative to the spectrometer optic view axis (axial/radial), provided by the invention as described, allows for optimum analytical figures of merit for almost all emission spectroscopic analysis applications which utilize a spectro-chemical source for sample excitation with a single instrument and thus improves the analytical capabilities of emission spectroscopy instruments beyond the current state of the art without the need of acquiring two dedicated instruments, resulting in a substantial cost saving for the end user It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An optical emission spectrometry instrument comprising an inductively coupled plasma generator (ICP) with an electromagnetic coil having a first connector and a second connector,
    wherein the electromagnetic coil is mounted to a mounting disk, and
    the first connector is coupled to a power output of a radio frequency power source, and
    the second connector is connected to the mounting disk, and further comprising:
    a spectro-chemical source for sample excitation, wherein the spectro-chemical source and the inductively coupled plasma generator have a longitudinal axis; and
    an optical system configured for viewing said spectro-chemical source with a fixed view axis,
    wherein the electromagnetic coil is mounted pivotably around one of the first or second connectors so that an orientation of the ICP is enabled to be altered from a first orientation of its longitudinal axis, which is parallel to the fixed view axis of the optical system, to a second orientation of its longitudinal axis, which is perpendicular to the fixed view axis of the optical system, and vice versa.

2. The optical emission spectrometer according to claim 1, wherein the electromagnetic coil is mounted pivotably around the first connector, and wherein the first connector is an input connector.

3. The optical emission spectrometer according to claim 2, wherein the second connector of the electromagnetic coil is a ground connector, which is electrically coupled to the mounting disk, and wherein the mounting disk has a sliding contact connected to the ground potential of the instrument.

4. The optical emission spectrometer according to claim 2, wherein the inductively coupled plasma generator is arranged on a rotatable disc, wherein the rotatable disc is configured to rotate around its center, wherein its center coincides with the coil input connector rotation axis.

5. The optical emission spectrometer according to claim 4, wherein the coupling of the input connector to the power output is a rotatable coupling allowing for a relative rotation of at least 90°.

6. The optical emission spectrometer according to claim 1, wherein the ICP is operated in argon at atmospheric pressure.

7. The optical emission spectrometer according to claim 1, wherein in the second orientation, in which the longitudinal axis is perpendicular to the fixed view axis of the optical system, a distance between the view axis and the coil equals the radius of the coil.

8. The optical emission spectrometer according to claim 1, wherein in the first orientation, the longitudinal axis coincides with the fixed view axis of the optical system.

9. A method of optical emission spectrometry, comprising:
- exciting a sample in a spectro-chemical plasma source of an inductively coupled plasma generator with an electromagnetic coil and a longitudinal axis to emit characteristic radiation, and
- observing the emitted characteristic radiation by an optical system having a fixed viewing axis,
- wherein an orientation of the inductively coupled plasma generator is enabled to be altered from a first orientation of its longitudinal axis, which is parallel to the fixed viewing axis of the optical system, to a second orientation of its longitudinal axis, which is perpendicular to the fixed view axis of the optical system, and vice versa, by swiveling the inductively coupled plasma generator around a pivot axis defined by the electromagnetic coil.

* * * * *